United States Patent
Smith (10) Patent No.: US 10,662,484 B1
(45) Date of Patent: May 26, 2020

(54) TWO UNIVERSAL DUPLEX PRIMER SETS AND A COMBINED REAL-TIME PCR AND HIGH RESOLUTION MELT ANALYSIS ASSAY FOR THE AMPLIFICATION OF GRAM-POSITIVE AND GRAM-NEGATIVE BACTERIA

(71) Applicant: Bench in a Box, LLC, New Glarus, WI (US)

(72) Inventor: Joshua A. Smith, New Glarus, WI (US)

( * ) Notice: Subject to any disclaimer, the term of this patent is extended or adjusted under 35 U.S.C. 154(b) by 282 days.

(21) Appl. No.: 15/468,454

(22) Filed: Mar. 24, 2017

Related U.S. Application Data (60) Provisional application No. 62/312,842, filed on Mar. 24, 2016.

(51) Int. Cl.
| | | |
|---|---|---|
| *C12Q 1/689* | (2018.01) | |
| *C12Q 1/6816* | (2018.01) | |
| *C12Q 1/686* | (2018.01) | |
| *C07H 21/04* | (2006.01) | |

(52) U.S. Cl.
CPC ............. *C12Q 1/689* (2013.01); *C12Q 1/686* (2013.01); *C12Q 1/6816* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,387,652 B1 | 5/2002 | Haugland et al. | |
| 7,294,466 B2 | 11/2007 | Mcmillian | |
| 8,323,898 B2 | 12/2012 | Niimi et al. | |
| 2004/0176584 A1 | 9/2004 | Terlesky | |
| 2005/0250146 A1 | 11/2005 | Mcmillian et al. | |
| 2006/0257871 A1 | 11/2006 | Chaubron et al. | |
| 2009/0061446 A1 | 3/2009 | Niimi et al. | |
| 2009/0258349 A1 | 10/2009 | Hristova et al. | |
| 2013/0196318 A1 | 8/2013 | O'hara et al. | |
| 2017/0191117 A1* | 7/2017 | Rand ...................... | C12Q 1/686 |

OTHER PUBLICATIONS

ATDBIO Catalog [retrieved on-line: www.atdbio.com/content/33/FAM-fluorescein-HEX-JOE-ROX-TAMRA-TET-Texas-Red-and-others; retrieval date: Apr. 15, 2019]. (Year: 2019).*
Huang et al. (Jan. 2011) "Multicolor Combinatorial Probe Coding for Real-Time PCR", J Plos One, 6(1): 1-10. (www.plosone.org).
Untergasser A, Cutcutache I, Koressaar T, Ye J, Faircloth BC, Remm M, Rozen SG (2012) "Primer3—new capabilities and interfaces", Nucleic Acids Research, 40(15):e115.
Koressaar T, Remm M (2007) "Enhancements and modifications of primer design program Primer3", Bioinformatics 23 (10)1289-9.1.
"Basics of Real-Time PCR" , Life Technologies, (2012), pp. 1-70, www.lifetechnologies.com.

* cited by examiner

*Primary Examiner* — Young J Kim
(74) *Attorney, Agent, or Firm* — Carrie M Stroup (57) ABSTRACT

Provided herein are biological assay mixtures for use in a real-time PCR and High Resolution Melt Analysis (HRMA) comprising: a universal Gram-positive forward and reverse primer pair; a universal Gram-negative forward and reverse primer pair; at least two biological probes, each one comprising a fluorophore, able to detect an amplicon prepared by the universal primer pairs; and an oligonucleotide intercalating dye for the HRMA. Methods for detecting a plurality of bacterial strains in the assay, comprise: contacting a biological sample with the biological assay mixture; preparing a plurality of amplicons for both Gram-positive and Gram-negative bacteria using one of the universal primer pairs; and detecting the amplicons using a plurality of biological probes comprising a fluorophore of one or more color emitters able to hybridize to known bacterial strains, wherein if no bacterial strain is identified, then determining whether Gram-positive and Gram-negative strains exist by using HRMA.

11 Claims, 5 Drawing Sheets

Specification includes a Sequence Listing.

Correct band size of approximately 250 base pairs

```
                            SEQUENCE LISTING

<160> NUMBER OF SEQ ID NOS: 15

<210> SEQ ID NO 1
<211> LENGTH: 17
<212> TYPE: DNA
<213> ORGANISM: Artificial Sequence
<220> FEATURE:
<223> OTHER INFORMATION: Gram-negative Forward Primer
      Primer/Probe/Quencher Sequence

<400> SEQUENCE: 1
tgcccgcttc ttctggc                                                  17

<210> SEQ ID NO 2
<211> LENGTH: 19
<212> TYPE: DNA
<213> ORGANISM: Artificial Sequence
<220> FEATURE:
<223> OTHER INFORMATION: Gram-negative Reverse Primer
      Primer/Probe/Quencher Sequence

<400> SEQUENCE: 2
gcaggccgag aatccactg                                                19

<210> SEQ ID NO 3
<211> LENGTH: 25
<212> TYPE: DNA
<213> ORGANISM: Artificial Sequence
<220> FEATURE:
<223> OTHER INFORMATION: Gram-positiveForward Primer
      Primer/Probe/Quencher Sequence

<400> SEQUENCE: 3
tgctactatt cgaaatgaaa tggca                                         25

<210> SEQ ID NO 4
<211> LENGTH: 33
<212> TYPE: DNA
<213> ORGANISM: Artificial Sequence
<220> FEATURE:
<223> OTHER INFORMATION: Gram-positiveForward Primer
      Primer/Probe/Quencher Sequence

<400> SEQUENCE: 4
gtatagttcg tcagctctga taatatttga gca                                33

<210> SEQ ID NO 5
<211> LENGTH: 29
<212> TYPE: DNA
<213> ORGANISM: Artificial Sequence
<220> FEATURE:
<223> OTHER INFORMATION: E. coli MG1655 detection probe
      Primer/Probe/Quencher Sequence

<400> SEQUENCE: 5
tgactggaat gccaattccg ctcaacagc                                     29

<210> SEQ ID NO 6
<211> LENGTH: 20
<212> TYPE: DNA
<213> ORGANISM: Artificial Sequence
```

```
<220> FEATURE:
<223> OTHER INFORMATION: P. aeruginosa detection probe
      Primer/Probe/Quencher Sequence

<400> SEQUENCE: 6
gcgcctgccg gtctcgcacc                                           20

<210> SEQ ID NO 7
<211> LENGTH: 27
<212> TYPE: DNA
<213> ORGANISM: Artificial Sequence
<220> FEATURE:
<223> OTHER INFORMATION: N. meningitidis detection probe
      Primer/Probe/Quencher Sequence

<400> SEQUENCE: 7
ggaaatgtct atcaggcgga aagtgcg                                   27

<210> SEQ ID NO 8
<211> LENGTH: 32
<212> TYPE: DNA
<213> ORGANISM: Artificial Sequence
<220> FEATURE:
<223> OTHER INFORMATION: E. coli O157:H7 detection probe
      Primer/Probe/Quencher Sequence

<400> SEQUENCE: 8
gaagagatga ttggcaaatt gactggaatg cc                             32

<210> SEQ ID NO 9
<211> LENGTH: 22
<212> TYPE: DNA
<213> ORGANISM: Artificial Sequence
<220> FEATURE:
<223> OTHER INFORMATION: S. typhimirium detection probe
      Primer/Probe/Quencher Sequence

<400> SEQUENCE: 9
cgcctgctgc tcaccaatcc gc                                        22

<210> SEQ ID NO 10
<211> LENGTH: 34
<212> TYPE: DNA
<213> ORGANISM: Artificial Sequence
<220> FEATURE:
<223> OTHER INFORMATION: A. baumannii detection probe
      Primer/Probe/Quencher Sequence

<400> SEQUENCE: 10
cggctccatc tcctgaagaa cttctagagc gtgc                           34

<210> SEQ ID NO 11
<211> LENGTH: 33
<212> TYPE: DNA
<213> ORGANISM: Artificial Sequence
<220> FEATURE:
<223> OTHER INFORMATION: S. aureus detection probe
      Primer/Probe/Quencher Sequence

<400> SEQUENCE: 11
cgagaagaca catagttctt cagggcgttc gcc                            33

<210> SEQ ID NO 12
<211> LENGTH: 34
<212> TYPE: DNA
<213> ORGANISM: Artificial Sequence
<220> FEATURE:
```

<223> OTHER INFORMATION: S. epidermidis detection probe
      Primer/Probe/Quencher Sequence

<400> SEQUENCE: 12
agacacacac atcttctgga agggtgccat ctga                                    34

<210> SEQ ID NO 13
<211> LENGTH: 25
<212> TYPE: DNA
<213> ORGANISM: Artificial Sequence
<220> FEATURE:
<223> OTHER INFORMATION: S. pyogenes detection probe
      Primer/Probe/Quencher Sequence

<400> SEQUENCE: 13
tggacggatg ccaagtccag ctggc                                              25

<210> SEQ ID NO 14
<211> LENGTH: 30
<212> TYPE: DNA
<213> ORGANISM: Artificial Sequence
<220> FEATURE:
<223> OTHER INFORMATION: E. faecalis detection probe
      Primer/Probe/Quencher Sequence

<400> SEQUENCE: 14
gggcgaatcc cctcaatggc tggttatcgt                                         30

<210> SEQ ID NO 15
<211> LENGTH: 36
<212> TYPE: DNA
<213> ORGANISM: Artificial Sequence
<220> FEATURE:
<223> OTHER INFORMATION: C. difficile detection probe
      Primer/Probe/Quencher Sequence

<400> SEQUENCE: 15
tcagcctcat acttctgcgg gtagagttcc atctga                                  36

TWO UNIVERSAL DUPLEX PRIMER SETS AND A COMBINED REAL-TIME PCR AND HIGH RESOLUTION MELT ANALYSIS ASSAY FOR THE AMPLIFICATION OF GRAM-POSITIVE AND GRAM-NEGATIVE BACTERIA

PRIORITY CLAIM

The present application claims priority to and benefit from U.S. Provisional Patent Application No. 62/312,842, titled "Method for Detection and Identification of Bacteria" and filed on Mar. 24, 2016 by JA Smith. The entire contents of the aforementioned application are herein expressly incorporated by reference.

COPYRIGHT NOTICE

A portion of the disclosure of this provisional patent application document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TRADEMARKS DISCLAIMER

The product names used in this document are for identification purposes only. All trademarks and registered trademarks are the property of their respective owners.

FIELD OF INVENTION

This invention relates to methods for the detection and identification of multiple strains of both Gram-positive and Gram-negative bacteria in one Real-Time Polymerase Chain Reaction (Real-Time PCR) and High Resolution Melt Analysis (HRMA) assay.

BACKGROUND OF THE INVENTION

Currently microbiological testing in the clinical setting relies on getting a primary culture on plate media, which will then undergo various identification testing and then antibiotic testing. This process usually takes a full 24-48 hours for the primary culture to grow large enough, then another 8-16 hours for antibiotic testing once the primary colony is large enough. For diseases, such as bacterial meningitis, this delay can be fatal within 24 hours of hospitalization, thus this time lapse makes current processes inadequate. Also, due to strain differences, the biochemical tests based upon the plate media can identify the bacteria as the wrong organism. Also, Gram staining, the gold standard of bacterial identification, can be difficult to properly do and can cause false identification. A more rapid and specific test is needed.

This invention is particularly helpful in the veterinary world when caring for large populations of animals. Currently it is impractical for ranch owners to test their entire herd for disease carriers. Instead of finding these carriers and performing targeted antibiotic therapy to only a few infected animals, most farmers and ranchers will treat the entire herd with antibiotics. This leads to increased resistance in the bacterial population as well as an increase in costs to market for the rancher. The molecular problem is that until now, in order to target multiple organisms, an individual primer/probe set was required for each target desired. This led to increasing assay complexity, false positives and decreased sensitivity the more targets that are assayed for, which the present invention overcomes.

A difficulty in developing assays for most real-time PCR thermocyclers is that most only have the ability to analyze up to four or five different color wavelengths. This has made multiplex assays at the clinical level meaningless. Only being able to assay at most 10 out of the 15-25 major bacterial species for each diagnostic sample media on a real-time PCR thermocycler was not worth the trouble due to the added costs of still being required to test for the rest of the bacterial species using the current standard culture method. It is for this reason that most Real-Time PCR machines are used for very specific assays for single organisms.

Researchers have tried to address the need for multiplexed bacteria detection. Most methods require a small amount of a primary culture, and then through various means are able to analyze the culture: by growth and/or biochemical tests (e.g., VITEK, Biomirieux): by analyzing chemical composition in a modified mass spectrometer (e.g., MALDI-TOF): by using antibodies paired to surface antigens (e.g., ELISA); or various other proprietary molecular probe based assays and equipment. All of these approaches have limitations, such as that they are only small scale and cannot be high-throughput, but the foremost being the requirement of a primary culture.

As a result, there exists the need for assays and methods for multiplexed detection of bacterial species, which are high-throughput, and able to test at least 40 strains of bacteria in one combined real-time PCR and HRMA assay with a run time of less than 4 hours.

SUMMARY OF THE INVENTION

Described herein is a method for amplifying a plurality (i.e. a large number) of Gram-positive and Gram-negative bacteria by adding DNA extracted from a patient specimen to a biological assay mixture and performing real-time PCR and High Resolution Melt Analysis. In one or more embodiments, the assay mixture comprises: two universal duplex primer sets, one for Gram-positive, and another for Gram-negative; and a plurality of DNA based biological probes that are used in different color combinations, wherein each probe is labelled with at least one fluorophore for detecting and identifying specific types of bacterial strains; and an intercalating dye that is used to label the amplicon for High Resolution Melt Analysis to identify remaining bacteria DNA sequences as Gram-negative or Gram-positive if no probe detects a bacteria strain during the real-time PCR, or if additional bacterial strains are present that the real-time PRC is unable to identify. The assay mixture of the duplex primer set and probes and the intercalating dye are used to identify the sample bacterial DNA in the specimen using a real-time thermos-cycler with a HRMA performed at the end of the amplification cycle. The HRMA is used as a fast method for determining the Gram type of the bacterial sample.

One aspect of the present invention is a rapid detection assay and method of detection of bacterial strains, the assay comprising: a first universal primer pair for detecting Gram-negative bacteria (e.g. SEQ ID NOS: 1, 2), and a second universal primer pair for detecting a Gram-positive bacteria (e.g. SEQ ID NOS: 3, 4).

Another aspect of the present invention, is a rapid detection assay and method of detection of bacterial strains, the assay comprising: DNA probes comprising at least one, or one or more, such as two, fluorescent dyes of different colors (e.g. FIG. 2, fluorophores blue and red in probe 4, and orange and red in probe 5). The use of probes comprising one or more fluorescent dyes in real-time PCR allows for up to 15 possible different bacterial strains (targets detected) in a 5 color real-time PCR thermocycler, and up to 30 possible different bacterial strains (targets detected) in a 6 color real-time PCR thermocycler.

Another aspect of the present invention is a rapid assay and a method to identify one or more bacterial strains simultaneously in a sample-specimen from a patient. In an embodiment, between 10 to 20, or 15 to 30, different types of bacterial strains within one sample can be identified in one assay.

Another aspect of the invention is if the rapid assay (real-time PCR) is not able to detect and identify at least one specific strain (type) of bacteria within the sample comprising one or more strains, then it can at least determine whether the unidentified strain(s) is/are Gram-positive or Gram-negative bacteria using an HRMA performed at the end of the real-time PCR amplification cycle.

Another aspect of the invention is even if the rapid assay (real-time PCR) is able to detect and identify some of the strains of bacteria within the specimen, it can at least determine whether the remaining unidentified strain(s) is/are Gram-positive or Gram-negative bacteria using an HRMA performed at the end of the real-time PCR amplification cycle Another aspect of the present invention is a method of running a detection assay within about 4 hours of the DNA extraction from the sample. The amount of time to extract DNA from a sample varies, e.g. 30 minutes to 2 hours, due to the extraction method used. Hence, using the presently disclosed identification assay and method, a lab can return within about 4.5 hours to 6 hours of receiving a patient specimen, a list of the bacterial strains within the specimen, or at a minimum whether the unidentified strains are Gram negative or Gram positive.

Another aspect is a method for detecting bacteria from a clinical sample, amplifying at least one of a first sequence of DNA in the clinical sample using a first set of universal primers, amplifying at least one of a second sequence of DNA in the sample using a second set of universal primers, detecting the amplified DNA using at least two sets of probes, where the at least two sets of probes have at least one fluorophore attached and the at least two sets of probes are capable of identifying Gram-negative and Gram-positive bacteria, and determining if the sample is positive for either Gram-negative bacteria or Gram-positive bacteria.

Another aspect of the present invention comprises kits that are drawn to reagents that can be used in practicing the methods disclosed herein. In particular, the kits can include any reagent or combination of reagents discussed herein or that would be understood to be required or beneficial in the practice of the disclosed methods. For example, the kits could include one or more primers, or primer-probe sets, disclosed herein to perform the extension, replication and amplification reactions discussed in certain embodiments of the methods, as well as the buffers and enzymes required to use the primes and probes as intended. The kits may further comprise: at least one biological probe comprising at least one fluorophore, wherein the biological probe is configured to detect an amplicon prepared by either the Gram-positive forward and reverse primer pair or by the Gram-negative forward and reverse primer pair; and at least one oligonucleotide intercalating dye able to be used in a High Resolution Melt Analysis (HRMA).

Other aspects of the invention will become apparent by consideration of the detailed description.

BRIEF DESCRIPTION OF THE DRAWINGS

The above and other features, aspects and advantages of various embodiments will become better understood with regard to the following description, appended claims, and accompanying drawings where:

DETAILED DESCRIPTION

Glossary of Terms and Phrases

As used herein, the term "primer" refers to a contiguous oligonucleotide sequence that is suitable for hybridizing, chain extension, and amplification in a real-time PCR reaction. The primers are for the detection of bacterial deoxyribonucleic acid (DNA), i.e. nucleic acids, nucleotides, polynucleotides, in a patient's sample, which requires a sufficient number of nucleotides to form a stable duplex, typically about 6-30 nucleotides, about 10-25 nucleotides and/or about 12-20 nucleotides.

As used herein, the phrase "a Gram-negative forward and reverse primer pair" refers to a first universal duplex primer pair (comprising or consisting of SEQ ID NO: 1 and 2, respectively), comprising a first and a second primer that hybridizes to opposite ends of a Gram-negative DNA, or nucleotide sequence, of Gram-negative bacteria in a patient specimen.

As used herein, the phrase "a Gram-positive forward and reverse primer pair" refers to a second universal duplex primer pair (comprising, or consisting essentially of, or consisting of SEQ ID NO: 3 and 4, respectively), comprising a third and a fourth primer that hybridize to opposite ends of a Gram-positive DNA or nucleotide sequence, of Gram-positive bacteria in a patient specimen.

As used herein, the term "amplicon" refers to a region of bacterial DNA that can be replicated using the universal primer pairs of the present invention (comprising, or consisting essentially of, or consisting of, SEQ ID NOS: 1-4).

As used herein, the term "probe" and "a biological probe" refer to a primer that is used for hybridization to the bacterial DNA. In one embodiment of the present invention, the probes are a fluoroprobe that comprise a fluorescent dye or fluorophore and a fluorescence quenching molecule that has been attached to a DNA oligo and is used to detect an amplicon prepared by either the universal Gram-positive forward and reverse primer pair, or the universal Gram-negative forward and reverse primer pair. Exemplary fluoroprobes comprise, by way of non-limiting examples: 6-FAM (NHS Ester), 6-FAM (Fluorescein), Fluorescein dT, Cy3™, TAMRA™, JOE (NHS Ester), Cy5™, TAMRA (NHS Ester), MAX (NHS Ester), TET™, Cy5.5™, ROX (NHS Ester), TYE™ 563, Yakima Yellow®, HEX, TEX 615, TYE™ 665, TYE 705, Texas Red®-X (NHS Ester), Alexa Fluor® 488 (NHS Ester), Alexa Fluor® 532 (NHS Ester), Alexa Fluor® 546 (NHS Ester), Alexa Fluor® 594 (NHS Ester), Alexa Fluor® 647 (NHS Ester), Alexa Fluor® 660 (NHS Ester), Alexa Fluor® 750 (NHS Ester), 5' IRDye® 700, 5' IRDye® 800, 5' IRDye® 800CW (NHS Ester), ATTO™ 488 (NHS Ester), ATTO™ 532 (NHS Ester), ATTO™ 550 (NHS Ester), ATTO™ 565 (NHS Ester), ATTO™ Rho101 (NHS Ester), ATTO™ 590 (NHS Ester), ATTO™ 633 (NHS Ester), ATTO™ 647N (NHS Ester), Rhodamine Green™-X (NHS Ester), Rhodamine Red™-X (NHS Ester), 5-TAMRA™ (Azide), WellRED D4 Dye, WellRED D3 Dye, WellRED D2 Dye, 6-FAM (Azide), Lightcycler® 640 (NHS Ester), Dy 750 (NHS Ester), CAL Fluor® Dyes, Pulsar®650 Dyes, Quasar® Dyes, SuperRox™, tetramethylrhodamine, carboxyrhodamine, carboxyrhodamine 6G, carboxyrhodol, carboxyrhodamine 110, conjugates thereof, and combinations thereof.

As used herein, the term "quenching molecule" refers to the molecule added to a fluorescent probe (the 3' end of a hydrolysis style probe) that blocks or "quenches" the fluorescent light that would normally be emitted by the fluorophore, this can be by either removing or joining the quencher to the fluorophore depending on the style of probe used. In one example, a hydrolysis style probe is used so that a quencher is placed opposite the fluorophore at the 3' end. During the extension phase of amplification, the DNA polymerase will break up the DNA probe thus freeing the fluorophore from the blocking of the quencher molecule and emitting light. Exemplary quenching molecules comprise, by way of non-limiting examples ZEN™-Iowa Black® FQ, Iowa Black® RQ, TAO™-Iowa Black® RQ.

In an embodiment, the fluoroprobe or fluorophore comprises 6-FAM.

As used herein, the term "intercalating dye" refers to the molecules that will bind to double stranded DNA. The dye/dsDNA complex will fluoresce when exposed to the appropriate excitation wavelength of light, which is dye dependent, and the intensity of the fluorescence may be proportionate to concentration of the dsDNA. High Resolution Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve (e.g. see FIG. 4).

Examples of such intercalating dyes for use in the mixture assay include, but are not limited to, SYBR Green-I®, SYBR Green-II®, SYBR Gold®, ethidium bromide, propidium iodide, EvaGreen® Dyes, LCGreen® Dyes, SYTO® Dyes, BEBO Dyes, BOXTO Dyes, Chromofy™ Dyes, raZor probes TOTO®-1 {Quinolinium, 1-1'-[1,3-propanediylbis[(dimethyliminio)-3,1-propanediyl]]bis[4-[(3-methyl-2 (3H)-benzothiazolylidene)methyl]]-, tetraiodide}, and YoPro® {Quinolinium, 4-[(3-methyl-2(3H)-benzoxazolylidene)methyl]-1-[3-(trimethylammonio)-propyl]-, diiodide}. Most preferred for the instant invention is a non-asymmetrical cyanide dye such as SYBR Green-I®, manufactured by Molecular Probes, Inc. (Eugene, Oreg.).

In an embodiment, the intercalating dye is SYBR Green-I®.

Method of making universal primers: The universal primers of the present invention (e.g. SEQ ID NOS: 1-4) were not designed to exactly match any individual bacterial DNA sequence. Instead they were designed using a consensus sequence for the most conserved regions of both lolB and hrcA bacterial genes. This consensus sequence is able to bind to the genomic bacterial DNA even if it is not an exact match to the gDNA, thus allowing it to be "universal", and specific enough to still target the correct regions.

Regions of 80% conserved were used to shorten the list of potential targets. Those remaining 6 pairs were then screened by non-routine experimentation to select the primer sets that worked the best at the annealing temperature of 47° C.

Provided herein are biological assay mixtures that use duplexed primer sets, biological probes comprising one or two different colored or more fluorophores, and, optionally, high-resolution melting analyses to detect and amplify bacterial species. During a first phase of the experiment, a technician could take a biological sample from a patient specimen, add the biological assay mixture, and analyze the sample on a real-time PCR thermocycler. The assay will amplify the target Gram-positive or Gram-negative bacteria using only the universal duplex primer sets (e.g. SEQ ID NOS: 1-4). During the amplification cycles, each of a plurality of probes for known Gram-negative bacteria (e.g. SEQ ID NOS: 5-10) and Gram-positive bacteria (e.g. SEQ ID NOS: 11-15) anneal to the correct sequence of a bacterial strain and the machine reads the fluorophore's emission, e.g. colored fluorescence. By using a combination of different colored fluorophores (e.g. 2) on the ends of some DNA probes in varying ratios instead of just one specific fluorophore, the user is able to test and detect multiple bacterial strains at a time. At the end of the real-time PCR amplification cycles, the sample is heated from 4° C. to 90° C. over a short amount of time (for example an increase of temperature around 1° C./second) to generate a high-resolution melting curve (i.e. a second experimental phase comprising HRMA with an intercalating dye or raZor like probe). This is so that if during the first phase of the experiment no probe based fluorescence is detected, the melting curve that is created can be used to identify bacterial DNA in the sample as at least either Gram-positive, Gram-negative or neither. Then even if the specific bacterial strain(s) infecting the patient are not detected, they can at least be administered a more targeted antibiotic response faster than current established methods.

Advantages of the this technology include, but are not limited to: faster identification of bacterial samples in a veterinary or clinical lab; shorter hospital stays; faster prescription of correct antibiotics leading to lower mortality/morbidity rates; quicker use of proper antibiotics and as a result reduced antibiotic resistance; repurposing existing equipment; eliminating the need for expensive, dedicated, one purpose machinery; greater accuracy than current standard biochemical tests; high throughput screening, enabling famers to screen entire herds and hospitals to process their samples faster; fewer technicians needed, reducing ongoing labor costs; increased capabilities of a hospital lab allowing for the potential of accepting samples and creating a new, positive revenue stream; and allowing smaller hospital labs to do their own testing with minimal equipment purchases.

Biological Assay Mixture

One aspect of the invention is a biological assay mixture. In one embodiment, the biological assay mixture comprises a universal Gram-positive forward and reverse primer pair; a universal gram-negative forward and reverse primer pair; at least one biological probe comprising a fluorophore, wherein the biological probe is configured to detect an amplicon prepared by either the Gram-positive forward and reverse primer pair or the Gram-negative forward and reverse primer pair; and an oligonucleotide intercalating dye.

The Gram-negative forward and reverse primer pair may be any primer pair configured to prepare an amplicon by amplifying an oligonucleotide sequence in Gram-negative bacteria. In certain embodiments, the Gram-negative forward and reverse primer pair is configured to prepare an amplicon of a portion of the lolB gene. In certain embodiments, the Gram-negative forward primer comprises, or consists essentially of, or consists of: SEQ ID NO:1 (5'-TGC CCG CTT CTT CTG GC-3'). In certain embodiments, the Gram-negative reverse primer comprises, or consists essentially of, or consists of: SEQ ID NO:2 (5'-GCA GGC CGA GAA TCC ACT G-3').

The Gram-positive forward and reverse primer pair may be any primer pair configured to prepare an amplicon by amplifying an oligonucleotide sequence in Gram-positive bacteria. In certain embodiments, the Gram-positive forward and reverse primer pair is configured to prepare an amplicon of a portion of the hrcA gene. In certain embodiments, the Gram-positive forward primer comprises, or consists essentially of, or consists of: SEQ ID NO:3 (5'-TGC TAC TAT TCG AAA TGA AAT GGC A-3'). In certain embodiments, the Gram-positive reverse primer comprises, or consists essentially of, or consists of: SEQ ID NO:4 (5'-GTA TAG TTC GTC AGC TCT GAT AAT ATT TGA GCA-3').

A surprising advantage of the present technology is that the assay mixture may comprise a biological probe that can identify specific bacterial species. Although certain genes are well enough conserved across a variety of species to allow for the use of forward and reverse primer pairs to prepare amplicons across the species, small variations within the oligonucleotides of the amplicons can be used to detect specific species by the association of the amplicon with a biological probe.

Certain biological probes are configured to detect an amplicon prepared by the gram-negative forward and reverse primer pair. In certain embodiments, the biological probe is configured to detect a Gram-negative bacterial species. Examples of biological probes configured to detect a Gram-negative bacterial species are provided in Table 1.

TABLE 1

| Gram-negative biological probes | | | |
|---|---|---|---|
| E. coli MG1655 | SEQ ID NO: 5 | 5'-/Fluorophore/TGA CTG GAA TGC CAA TTC CGC TCA ACA GC/Quencher/ -3' |
| P. aeruginosa | SEQ ID NO: 6 | 5'-/Fluorophore/GCG CCT GCC GGT CTC GCA CC/Quencher/-3' |
| N. meningitidis | SEQ ID NO: 7 | 5'-/Fluorophore/GGA AAT GTC TAT CAG GCG GAA AGT GCG/Quencher/ -3' |
| E. coli O157:H7IShigela | SEQ ID NO: 8 | 5'- /Fluorophore/GAA GAG ATG ATT GGC AAA TTG ACT GGA ATG CC/Quencher/-3' |
| S. typhimirium | SEQ ID NO: 9 | 5'-/Fluorophore/CGC CTG CTG CTC ACC AAT CCG C/Quencher/-3' |
| A. baumannii | SEQ ID NO: 10 | 5'-/Fluorophore/CGG CTC CAT CTC CTG AAG AAC TTC TAG AGC GTG C/Quencher/-3' |

Other Gram-negative species that may also be detected using the assay and method of the present invention include, but are not limited to, those described in Table 2.

TABLE 2

| Bacterial species targeted by Gram-negative primer pair | |
|---|---|
| Legionella pneumophila | Salmonella sp. |
| Acinetobacter baumannii | Shigella sp. |
| Pseudomonas fluorescens | Pseudomonas aeruginosa |
| Klebsiella pneumonia | Klebsiella oxytoca |
| Neisseria gonorrhoeae | Neisseria meningitidis |
| Enterobacter cloacae | Enterobacter aerogenes |
| Serratia marcescens | Bordetella sp. |
| Escherichia coli O157:H7 | Vibrio vulnificus |
| Vibrio parahaemolyticus | Vibrio cholerae |
| Yersinia enterocolitica | Yersinia pestis |
| Proteus mirabilis | Haemophilus influenzae |
| Haemophilus ducreyi | Haemophilus parasuis |
| Edwardsiella tarda | Campylobacter. jejuni |

Certain other biological probes are configured to detect an amplicon prepared by the Gram-positive forward and reverse primer pair. In certain embodiments, the biological probe is configured to detect a Gram-positive bacterial species. Examples of biological probes configured to detect a Gram-positive bacterial species are provided in Table 3.

TABLE 3

Gram-positive biological probes

| | | |
|---|---|---|
| S. aureus | SEQ ID NO: 11 | 5'-/Fluorophore/CGA GAA GAC ACA TAG TTC TTC AGG GCG TTC GCC/Quencher/-3' |
| S. epidermidis | SEQ ID NO: 12 | 5'-/Fluorophore/AGA CAC ACA CAT CTT CTG GAA GGG TGC CAT CTG A/Quencher/-3' |
| S. pyogenes | SEQ ID NO: 13 | 5'-/Fluorophore/TGG ACG GAT GCC AAG TCC AGC TGG C/Quencher/-3' |
| E. faecalis | SEQ ID NO: 14 | 5'-/Fluorophore/GGG CGA ATC CCC TCA ATG GCT GGT TAT CGT/Quencher/-3' |
| C. difficile | SEQ ID NO: 15 | 5'-/Fluorophore/ TCA GCC TCA TAC TTC TGC GGG TAG AGT TCC ATC TGA/Quencher/-3' |

Other Gram-positive species that may also be detected include, but are not limited to, those described in Table 4.

TABLE 4

Bacterial species targeted by Gram-positive primer pair

| | |
|---|---|
| S. pneumonia | L. monocytogenes |
| B. anthracis | B. Cereus |
| E. faecalis | E. faecium |
| S. agalactiae | S. pyogenes |
| C. botulinum | C. difficile |
| M. tuberculosis | S. epidermidis |
| S. aureus | |

In certain embodiments, the biological probe comprises a plurality of biological probes, wherein the plurality of biological probes comprises a plurality of fluorophores. In certain embodiments, the biological probe comprises two or more fluorophores, wherein the two or more fluorophores have resolvable distinct emission wavelengths. The possibility of preparing probes having more than one fluorophore allows for the multiplexed detection of bacterial special.

Detection of a biological target is achieved by using a duplex primer set, fluorescent probes and, optionally, a high-resolution melting analysis (HRMA). A technician would take a biological sample, contact the biological sample with the biological assay mixture, and run it on a real-time PCR thermocycler. The assay will amplify the target Gram-positive or Gram-negative bacteria using only the duplex primer set. During the amplification cycles a biological probe anneals to the correct sequence and the machine reads the emission wavelength, e.g. fluorescence wavelength. By using a combination of different fluorophores on the 5' or 3' end of some DNA probes in varying ratios instead of just one specific chromophore allows for detection of multiple targets at the same time. In certain embodiments, the chromophore is a fluorophore.

A surprising advantage of the present invention is the result of using multiple kinds of fluorophores on the 5' or 3' end of the probe for the same target. This allows for $2^{(n-1)}-1$ different targets. And, the present invention has the advantage of using only a duplex primer set to analyze all Gram-negative and Gram-positive bacteria of clinical importance. These differences allow the assay to analyze more targets than the readable emission wavelengths of the detector and they eliminate the complications of current large multiplex assays.

The different probe styles and fluorophore chemistries of the present invention do not matter, so any probe or fluorophore can be adapted to be used with the presently disclosed assay, including hydrolysis, hybridization and molecular beacon style probes. And, with the increased sensitivity of the assay there is no need for a primary culture. If bacterial DNA is amplified but the correct probe is not present in the assay, then high-resolution melting analysis run at the end of the assay can be used to detect if the causative organisms are either Gram-positive or Gram-negative in order to treat the patient appropriately, while secondary tests are performed to identify the bacterial strains.

Kits for Real Time PCR and HRMA

Disclosed herein are kits that are drawn to reagents that can be used in practicing the methods disclosed herein. In particular, the kits can include any reagent or combination of reagents discussed herein or that would be understood by one of skill in the art to be required or beneficial in the practice of the disclosed methods. For example, the kits could include one or more primers, or primer-probe sets, disclosed herein to perform the extension, replication and amplification reactions discussed in certain embodiments of the methods, as well as the buffers and enzymes required to use the primers or primer-probe sets as intended.

In an embodiment, the kits are drawn to reagents that can be used in practicing the methods of detecting multiple bacterial strains in one or more real-time PCR and HRMA experiments, as disclosed herein. For example, the kits could include one or more primers, or prime-probe sets, comprising, consisting essentially of, or consisting of: SEQ ID NOS: 1-4, or at least one of SEQ ID NOS: 1-4, to perform the extension, replication and amplification reactions discussed in certain embodiments of the methods, as well as the buffers and enzymes required to use the primers as intended. The kits may further comprise: at least one biological probe comprising at least one fluorophore, wherein the biological probe is configured to detect an amplicon prepared by either the Gram-positive forward and reverse primer pair or by the Gram-negative forward and reverse primer pair; and at least one oligonucleotide intercalating dye able to be used in a High Resolution Melt Analysis (HRMA).

Within the kit, each biological probe: 1) is configured to detect a bacterial species selected from the group consisting of E. coli MG1655, P. aeruginosa, N. meningitidis, E. coli O157:H7/Shigella, S. typhimirium, and A. baumannii; and/or 2) wherein each biological probe comprises an oligonucleotide sequence consisting of one of: SEQ ID NOS: 5-10, or selected from the group consisting of SEQ ID NO: 5, SEQ ID NO: 6, SEQ ID NO: 7, SEQ ID NO: 8, SEQ ID NO: 9, and SEQ ID NO: 10. And/or within the kit, each biological probe: 1) is configured to detect a bacterial species selected from the group consisting of S. aureus, S. epidermidis, S. pyogenes, E. faecalis, and C. difficile; and/or wherein each biological probe comprises a continuous oligonucleotide sequence consisting of one of: SEQ ID NOS: 11-15, or selected from the group consisting of SEQ ID NO: 11, SEQ ID NO: 12, SEQ ID NO: 13, SEQ ID NO: 14, and SEQ ID NO: 15. And/or within the kit, each biological probe comprises: 1) at least one fluorophore emitting light at a distinct emission wavelengths; and 2) wherein when the biological probe comprises two or more fluorophores, the fluorophores have resolvable distinct emission wavelengths.

The kits may further comprise a real-time PCR and HRMA kit for detecting multiple types of Gram-positive and Gram-negative strains of bacteria simultaneously, and comprising the primer or primer-probe sets disclosed herein, and instructions for interpreting results.

The present invention further comprises a method, kits, compositions, and primer-probe complexes for detecting bacteria comprising contacting a biological sample with a biological assay mixture; preparing an amplicon with a first oligonucleotide sequence in the clinical sample using a Gram-negative forward and reverse primer pair or a Gram-positive forward and reverse primer pair; and detecting the amplicon using a biological probe comprising at least one fluorophore, wherein the biological probe is configured to detect an amplicon prepared by either the Gram-positive forward and reverse primer pair or the Gram-negative forward and reverse primer pair. The method may further comprise determining if the sample is positive for either Gram-negative bacteria or Gram-positive bacteria.

In some embodiments, the method may further comprise running a High-Resolution Melt Analysis (HRMA) to further identify the presence of Gram-negative bacteria and Gram-positive bacteria in the clinical sample. At the end of the amplification the sample may be optionally heated from 4° C. to 100° C. to generate a high-resolution melting curve. This is so that if during the test DNA is amplified, but no probe based emission wavelengths are detected, then the melting curve that is created can be used to identify the bacteria as either Gram-positive or Gram-negative. Although the bacterial species will not be affirmatively identified, knowledge of whether the bacteria are Gram-positive or negative still allows for a targeted antibiotic response.

DNA base pairs bond together is a specific way. Guanine binds to Cytosine and Adenine binds to Thymine. The thermodynamic stability of these pairings differs due to the amount of atomic bonds created between the molecules (A-T has 2 bonds, G-C has 3). This affects the amount of energy that is required to be applied to separate the base pair. A-T base pairs, therefore, require less energy applied to separate than G-C base pairs. This is relevant due to Gram-negative bacteria having a higher percentage of G-C base pairs in their DNA than Gram-positive bacteria. Due to this difference in GC % in each amplicon, the products or each primer pair will melt at very different temperatures giving peaks in different regions. Whichever region the product curve appears in will identify the bacteria as either Gram-positive or Gram-negative. Using the HRMA at the end of the real-time PCR cycle in this way allows for the assay to pick up strange or exotic bacteria not normally expected in the normal assay.

The following is provided as an example to further illustrate the technology. If a machine can only read 3 different emission wavelengths (e.g., red, blue and green), a user will be able to detect three distinct biological targets at the same time as well as detect other unexpected targets. The biological assay mixture may comprise: a Gram-negative forward primer, a Gram-negative reverse primer, a Gram-positive forward primer, a Gram-positive reverse primer, a first biological probe comprising a fluorophore that emits a red wavelength and that detects a first biological target, a second biological probe that emits a blue wavelength and that detects a second biological target, a third biological probe that will detect a third biological target and will compromise of a DNA sequence and ½ of the total added third probe will have a fluorophore that emits a red wavelength and ½ of the total added amount of the third probe will have a fluorophore that emits a blue wavelength, and a DNA intercalating dye for high-resolution melting curve analysis. An illustration of the biological probes of this example are provided in FIG. 1.

Figure 1:
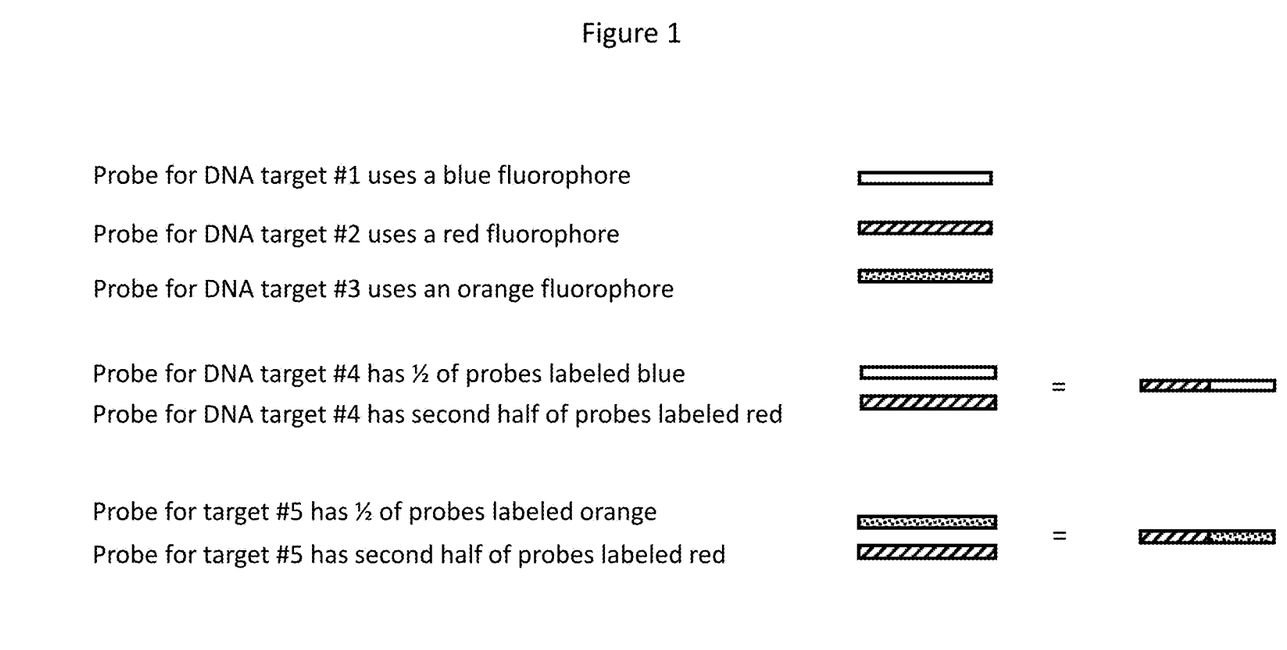
FIG. 1 illustrates how the present invention bypasses the color limit of a Real-Time PCR (real-time PCR) thermocycler. By using multiple probes in combination, it enables the assay to have individual "finger prints" for faster identification, and it allows for up to 15 possible targets in a 5 color real-time PCR thermocycler and up to 30 possible targets in a 6 color real-time PCR thermocycler.

FIG. 1 further illustrates an example of how a user can identify 5 different bacterial DNA targets using only 3 different colored fluorophores using 4 hydrolysis probes. The 1 unit of the first 3 DNA probes are added comprising: Probe 1 (5'-/Fluorophore1/DNA Target1/Quencher/-3'); Probe 2 (5'-/Fluorophore2/DNA Target2/Quencher/-3'); and, Probe 3 (5'-/Fluorophore3/DNA Target3/Quencher/-3'). For the $4^{th}$ and $5^{th}$ targets, instead of using 1 unit of a single $4^{th}$ and $5^{th}$ colored fluorophores, each has 2 DNA probes made and 0.5 units of these are added. The DNA sequence and the 3' Quencher are the same, but the fluorophore on the 5' end changes. One is produced that contains Fluorophore 1 and one that contains Fluorophore 2 for Probe target 4; and Fluorophore 2 and Fluorophore 3 for Probe target 5; and these are added in 50/50 ratios. For example: Target 4 uses Probe 4 (5'-/Fluorophore1/DNA Target4/Quencher/-3'), and Probe 4 (5'-/Fluorophore2/DNA Target4/Quencher/-3') in a 50/50 ratio and Target 5 uses Probe 5 (5'-/Fluorophore2/DNA Target5/Quencher/-3'), and Probe 5 (5'-/Fluorophore3/DNA Target5/Quencher/-3') in a 50/50 ratio.

The biological assay mixture will be contacted with a biological sample, and the emission results would then be interpreted in the following manner: if only red emission is detected, then the biological sample is positive for the first target; if only the blue emission is detected, then the biological sample is positive for the second target; and if both red and blue emission is detected, then the biological sample is positive for the third target. An illustration of the possible time-resolved emission spectra are provided in FIG. 3.

Figure 2:
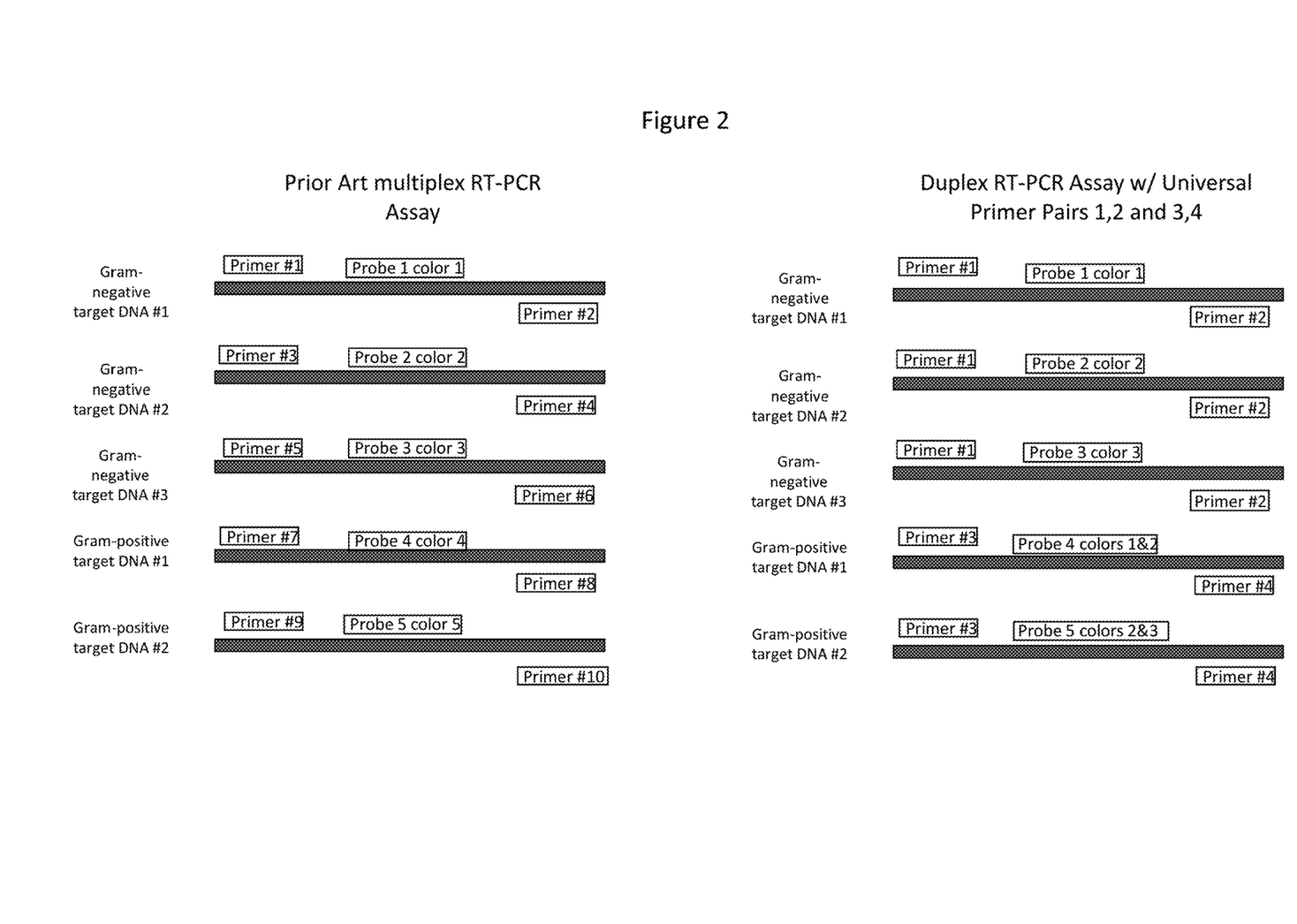
FIG. 2 shows a comparison of complexity of the prior art multiplex real-time PCR and the method of the present invention.

FIG. 2 illustrates a visual comparison of an assay that would identify 5 different targets using conventional multi-plex RT-PCR methods (left) and the Universal Duplex RT-PCR method described in the present disclosure(right). In conventional multi-plex RT-PCR assays, every DNA target that needs to be amplified requires its own individual forward and reverse primer set as well as the DNA probe required for identification. Using the novel universal duplex real-time-PCR method disclosed herein, only 2 universal forward and reverse primer sets are needed (2 compared to 5 in this example). This greatly simplifies the assay and significantly reduces the many problems that occur with complex multiplex assays, such as the amplification of nonsense side products.

In an embodiment, amplification primers and detection probes for use in the present invention are selected using Primer3 software and ordered from Integrated DNA Technologies (see Untergasser A, Cutcutache I, Koressaar T, Ye J, Faircloth B C, Remm M, Rozen S G (2012) Primer3-new capabilities and interfaces. *Nucleic Acids Research* 40(15): e115; Koressaar T, Remm M (2007) Enhancements and modifications of primer design program *Primer3 Bioinformatics* 23(10):1289-91).

Figure 3:
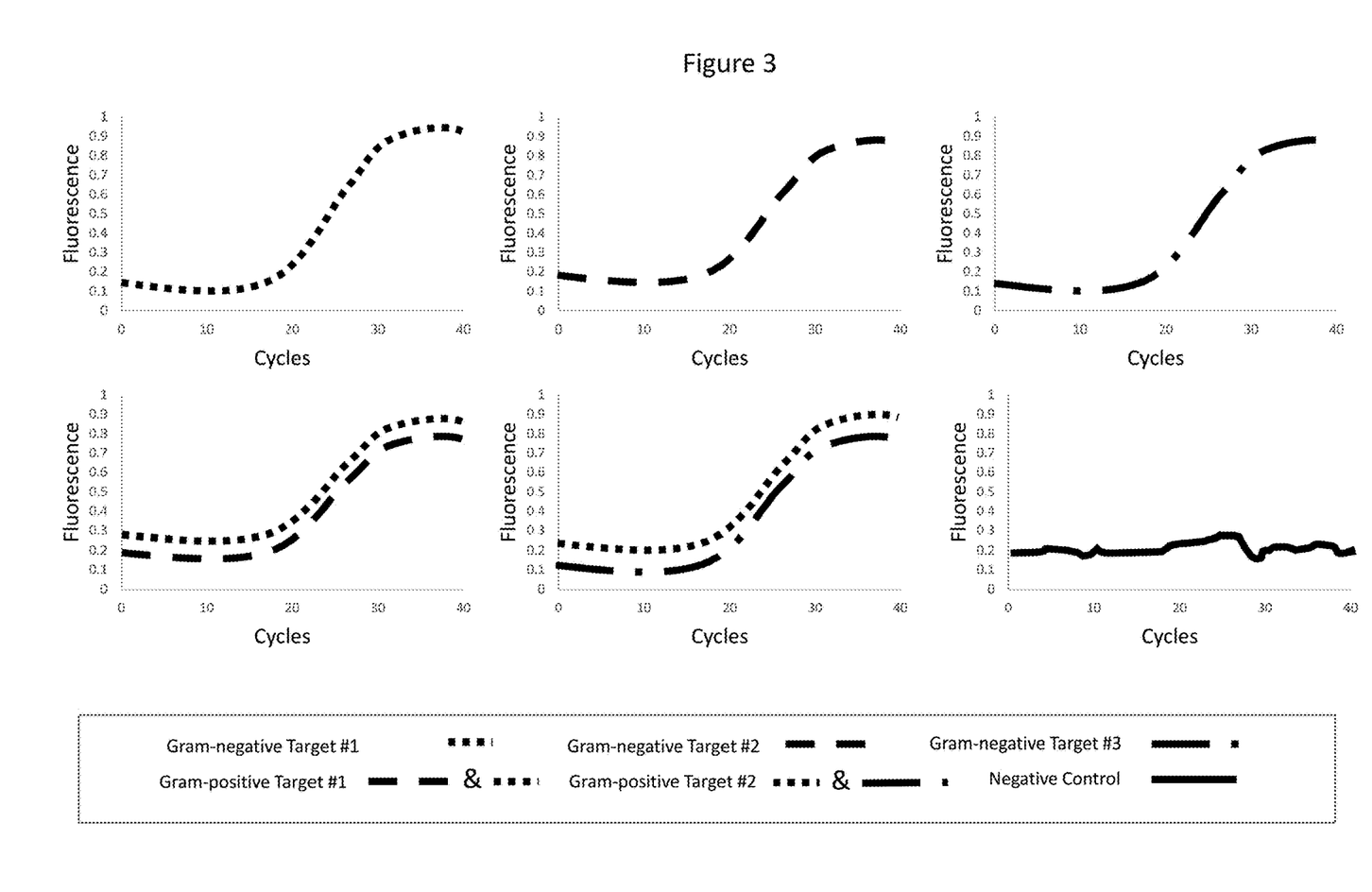
FIG. 3 shows examples of what positive test results would look like when testing three Gram-negative and two Gram-positive bacteria in this assay.

FIG. 3 illustrates an example of what the results would look like for a theoretical real-time PCR assay using universal duplex primer sets and DNA based probes with fluorophores in combinations. In this example, positive amplification of *S. aureus*, *E. coli* MG1655 and *S. epidermidis* is the standard single positive amplification curve. Conversely, *C. difficile* and *E. coli* O157:H7 have identification probes with 2 different fluorophores in a 50/50 ratio. This leads to 2 amplification curves when a sample is positive for these bacteria.

In the event that no emission is detected, a user may optionally perform high-resolution melt analysis (HRMA) by heating the sample from 4° C. to 90° C. at a measurable rate (such as 0.5° C./second) after the completion of the amplification phase of the real-time-PCR. This generates a high-resolution melting curve that exploits the thermodynamic differences in the A-T and G-C base pairs by measuring the amount of intercalating dye that is release over the course of the HRMA. This can identify whether a sample is Gram-positive or Gram-negative because Gram-negative bacteria have a higher GC % which roughly translates to more thermodynamically stable DNA in which the DNA strands do not separate (or melt) until at a higher temperature as compared to Gram-positive bacterial DNA. This allows the user to be able to determine if the DNA sample is Gram-positive or Gram-negative, but not to be able to identify the specific bacterial strain that the DNA sample is from. (e.g. Tables 2 and 4).

Figure 4:
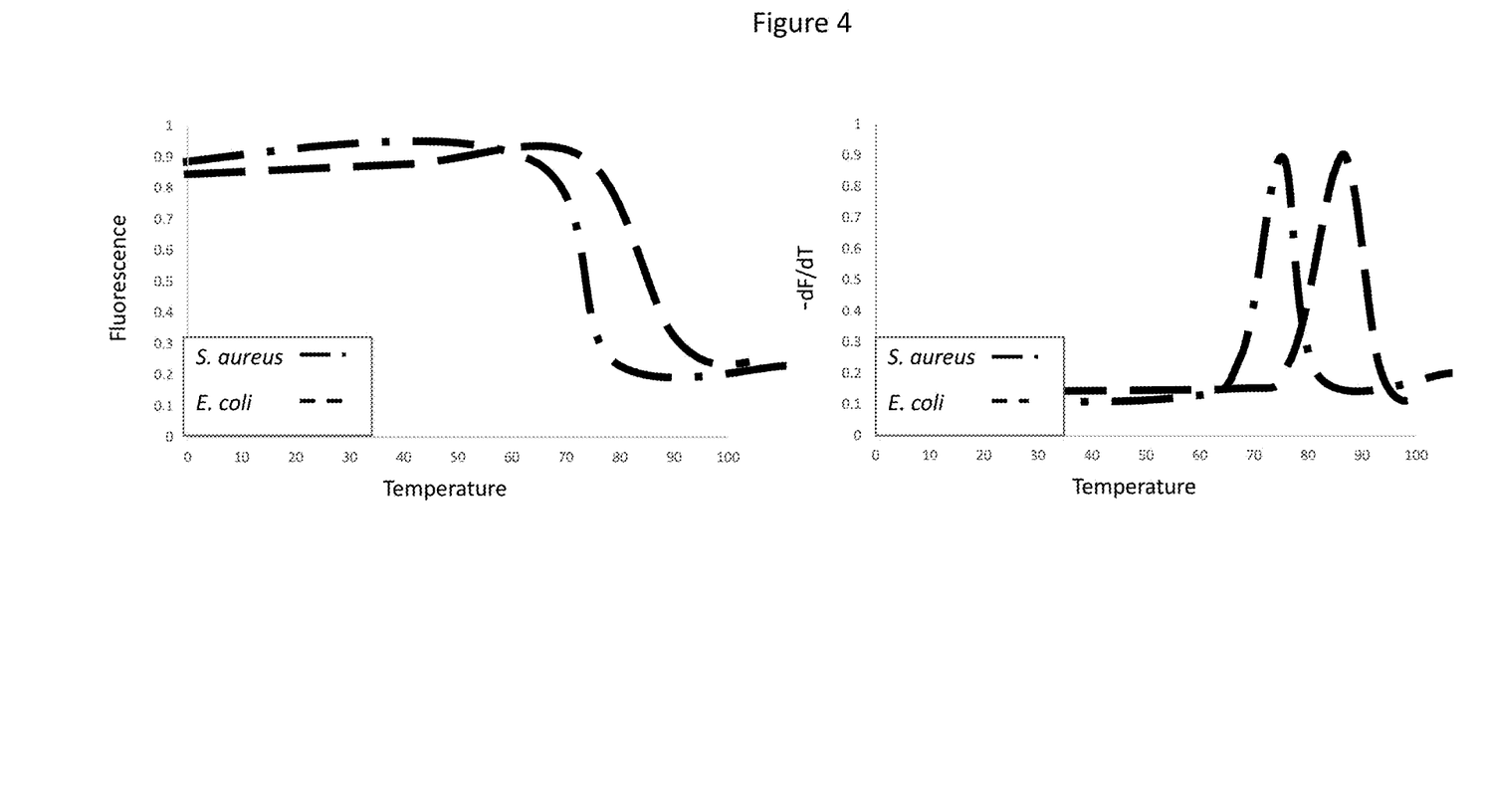
FIG. 4 illustrates an example of how the HRMA portion of the assay is able to determine if a bacterial DNA sample is Gram-positive or Gram-negative.

FIG. 4 shows the results of an example HRMA assay between to DNA samples, one Gram-positive, and one Gram-negative. *E. coli* MG1655 is a Gram-negative bacterium and therefore it's DNA will have a higher melting temperature than the DNA of a Gram-positive bacterium such as *S. aureus*. This is shown by the graph on the left of FIG. 4 showing the steep drop in fluorescence as the temperature increases. The derivative of this graph is show on the right of FIG. 4 making it easier to see by turning the slope into a distinct peak.

In FIG. 4, as the temperature is increased from 4° C. to 100° C. at a rate of 1° C./second, the amplified DNA product begins to separate (melt) and release the intercalating dye. At a certain point a majority of the DNA product separates and creates a large decrease in fluorescence. This is the melting temperature of the amplified DNA product. The amplified DNA products of Gram-positive and Gram-negative bacteria will be different due to the GC % difference in the two types of bacteria. High GC % (Gram-negative bacteria) DNA is more stable than low GC % (Gram-positive) DNA and therefore will have a higher melting temperature. This figure shows an example comparing the different melting temperatures of *E. coli* and *S. aureus*. *E. coli* has a GC % of approximately 53% compared to *S. aureus* which has a GC % of 38% in this amplified product.

EXEMPLIFICATION

Primer and Probe selection: Amplification primers and detection probes were selected using Primer3 software (primer3.ut.ee) and ordered from Integrated DNA Technologies (see Untergasser A, Cutcutache I, Koressaar T, Ye J, Faircloth BC, Remm M, Rozen SG (2012) Primer3-new capabilities and interfaces. *Nucleic Acids Research* 40(15): e115; Koressaar T, Remm M (2007) Enhancements and modifications of primer design program Primer3, *Bioinformatics* 23(10):1289-91).

Multiple Sequence Alignments: Pairwise multiple sequence alignments were performed using Clustal Omega from EMBL-EBI. Proof of concept testing using a duplex primer set to amplify DNA from four different Gram-negative bacteria and three different Gram-positive bacteria was achieved with the following cycling parameters: a 5:00 minute initial denaturation step at 95° C. followed by 35 cycles of 0:20 sec denaturation step of 95° C. and a 0:20 sec annealing/extension step at 47° C.

DNA Extraction: Bacterial chromosomal DNA was extracted from an overnight LB broth culture by a QIAmp DNA Mini Kit (Qiagen).

The Gram-positive universal primer pair (SEQ ID NOS: 3, 4) and the Gram-negative universal primer pair (SEQ ID NOS: 1, 2) were added into an assay mixture.

PCR Reactions: 20 µl reactions contained final concentrations of 0.25 units of Taq DNA polymerase (NEB), 1x supplied Polymerase buffer, 0.125 µM Gram-negative Forward Primer (SEQ ID NO: 1), 0.25 µM Gram-negative Reverse Primer (SEQ ID NO: 2), 0.125 µM Gram-positive Forward Primer (SEQ ID NO: 3), 0.25 µM Gram-positive Reverse Primer (SEQ ID NO: 4), 2.5 mM dNTPs, 2 mM MgCl2, and 35 ng/µl of DNA, and 5 µl of an enhancement reagent (5M Betaine, 50% DMSO (w/v) 80% glycerol (w/v)). PCR cycling was performed with a 5:00 minute initial denaturation step at 95° C. followed by 35 cycles of 0:20 sec denaturation step of 95° C. and a 0:20 sec annealing/extension step at 47° C. The cycle was ended with a 4° C. hold.

Figure 5:
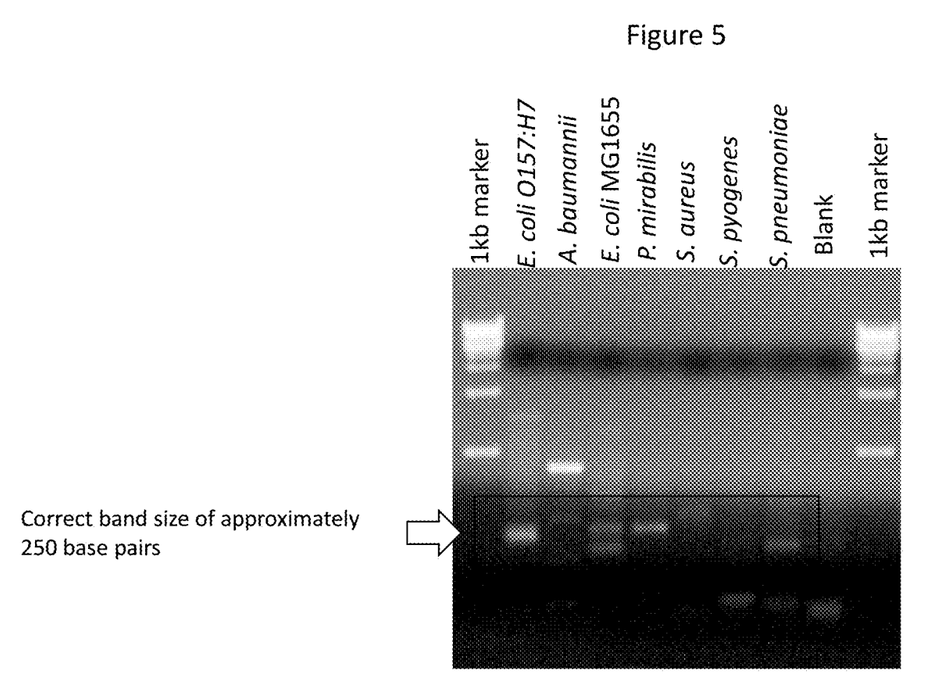
FIG. 5 illustrates the results of a proof of concept duplex PCR that is able to amplify four different Gram-negative bacteria and three different Gram-positive bacteria using the same reaction conditions for each.

The results of this experiment showing the amplification of the four Gram-negative bacteria and the amplification of the three Gram-positive bacteria are presented in FIG. 5, which is an image of a 1× TBE (Fisher Scientific) agarose gel (1% (w/v)) stained by adding 5 µl of EtBr directly to the gel when casting. The gel was run in 1× TBE (Fisher Scientific) for 45 minutes at approximately 3 V/cm and viewed on a UV transilluminator. Seven different bacterial strains were tested for: *E coli* 0157:H7; *A. baumannii*; *E. coli* MG1655; *P. mirabilis*; *S. aureus*; *S. pyogenes*; and *S. pneumoniae*. Correct positive band size of approximately 250 base pairs is highlighted to illustrate that *E. coli* O157: H7 (Gram-negative), *P. mirabilis*, (Gram-negative), and *S. aureus* (Gram-positive) were detected concurrently from one real-time PCR result using the universal Gram-positive and Gram-negative primer pairs disclosed herein.

HRMA is performed immediately following the final amplification step of the RT-PCR assay. The samples were cooled to 10° C., then the temperature was increased at rate of 1° C./second to a final temperature of 90° C.

It is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

The use of "including," "comprising," or "having" and variations thereof herein is meant to encompass the items listed thereafter and equivalents thereof as well as additional items. As used here and in the claims, singular articles such as "a" and "an" and "the" and similar references in the context of describing the elements (especially in the following claims) are to be construed to cover both the singular and the plural, unless otherwise indicated herein or clearly contradicted by context. Similarly, when the plural form is used it is to be construed to cover the singular form as the context permits. The use of any and all examples, or exemplary language (e.g., "such as") is intended to better illuminate the embodiments and does not pose a limitation on the scope of the claims unless otherwise stated.

As used herein, the term "about" or "approximately" means within 20%, preferably within 10%, and more preferably within 5% of a given value or range.

While specific embodiments have been described, various changes and substitutions may be made without departing from the scope of the invention. Therefore, the invention described here should not be limited except by the following claims and their equivalents. Those skilled in the art will recognize, or be able to ascertain using no more than routine experimentation, many equivalents to the specific embodiments of the invention described herein. Such equivalents are intended to be encompassed by the following claims.

What is claimed is:

1. A biological assay mixture for multiplexed bacterial strains detection, comprising:
   (a) a universal Gram-positive forward and reverse primer pair comprising SEQ ID NO: 3 and 4, respectively;
   (b) a universal Gram-negative forward and reverse primer pair comprising SEQ ID NO: 1 and 2, respectively;
   (c) at least two biological probes comprising at least one fluorophore each, wherein at least one biological probe comprises a sequence selected from SEQ ID NOS: 11-15 that is configured to detect an amplicon of the gene hrcA prepared by the Gram-positive forward and reverse primer pair, and at least one biological probe comprises a sequence selected from SEQ ID NOS: 5-10 that is configured to detect an amplicon of the gene lolB prepared by the Gram-negative forward and reverse primer pair;
   (d) at least one oligonucleotide intercalating dye able to be used in a High Resolution Melt Analysis (HRMA);
   wherein the biological assay mixture is able to identify a plurality of a Gram-positive and Gram-negative bacterial strains concurrently in a Real-Time Polymerase Chain Reaction (PCR); and
   if the Real-Time PCR fails to identify a bacterial strain, the biological assay mixture is still able to detect the presence of a plurality of Gram-positive and Gram-negative bacteria strains within a patient's specimen by HRMA analysis.

2. The biological assay mixture of claim 1, wherein the Gram-negative forward primer consists of the oligonucleotide sequence of SEQ ID NO:1 (5'-TGC CCG CTT CTT CTG GC-3'), and the Gram-negative reverse primer consists of the oligonucleotide sequence of SEQ ID NO:2 (5'-GCA GGC CGA GAA TCC ACT G-3').

3. The biological assay mixture of any of claim 1, wherein the Gram-positive forward primer consists of the oligonucleotide sequence of SEQ ID NO:3 (5'-TGC TAC TAT TCG AAA TGA AAT GGC A-3'), and the Gram-positive reverse primer consists of the oligonucleotide sequence of SEQ ID NO:4 (5'-GTA TAG TTC GTC AGC TCT GAT AAT ATT TGA GCA-3').

4. The biological assay mixture of claim 1, wherein the at least two biological probes comprise,
   (a) at least one probe with one fluorophore emitting light at a distinct emission wavelength; and
   (b) at least one probe with two or more fluorophores, wherein the fluorophores have resolvable distinct emission wavelengths.

5. The biological assay of claim 1, wherein the at least one fluorophore is 6-FAM.

6. A method for detecting multiple bacterial strains of both Gram-positive and Gram-negative bacteria in one assay comprising a Real-Time Polymerase Chain Reaction (Real-Time PCR) and a High Resolution Melting Analysis (HRMA) experiment, the method steps comprising:
  (a) contacting a biological sample from a patient specimen with a biological assay mixture, wherein the biological assay mixture comprises,
    a universal Gram-positive forward and reverse primer pair comprising SEQ ID NO: 3 and 4, respectively;
    a universal Gram-negative forward and reverse primer pair comprising SEQ ID NO: 1 and 2, respectively;
    at least two biological probes comprising at least one fluorophore each, wherein at least one biological probe comprises a sequence selected from SEQ ID NOS: 11-15 that is configured to detect an amplicon of the gene hrcA prepared by the Gram-positive forward and reverse primer pair, and at least one biological probe comprises a sequence selected from SEQ ID NOS: 5-10 that is configured to detect an amplicon of the gene lolB prepared by the Gram-negative forward and reverse primer pair;
    at least one oligonucleotide intercalating dye able to be used in a High Resolution Melt Analysis (HRMA);
  (b) identifying a plurality of Gram-positive and Gram-negative bacterial strains concurrently with the at least two biological probes during the first phase of the experiment comprising a Real-Time Polymerase Chain Reaction (PCR); and,
  (c) if the Real-Time PCR fails to identify at least one bacterial strain, then detecting the presence of a plurality of Gram-positive and Gram-negative bacterial strains within the biological sample during the second phase of the experiment using HRMA and the at least one oligonucleotide intercalating dye.

7. The method for detecting multiple bacterial strains of claim 6, wherein step (b) further comprises,
  preparing a plurality of bacterial amplicons using the real-time PCR from the biological sample using the universal Gram-negative forward and reverse primer pair comprising a contiguous oligonucleotide sequence of SEQ ID NO: 1 and 2, respectively, and the universal Gram-positive forward and reverse primer pair comprising a contiguous oligonucleotide sequence of SEQ ID NO: 3 and 4, respectively;
  detecting the plurality of amplicons using the biological probes comprising at least one colored fluorophores, wherein the biological probes are configured to detect the amplicons prepared by the Gram-positive forward and reverse primer pair and the Gram-negative forward and reverse primer pair; and,
  identifying the plurality of bacterial strains, wherein each biological probe comprises a contiguous oligonucleotide sequence from a Gram-negative or Gram-positive bacterial strain selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, and SEQ ID NO: 15.

8. The method for detecting multiple bacterial strains of claim 6, wherein the fluorophores are 6-FAM.

9. The method for detecting multiple bacterial strains of claim 6, wherein the intercalating dye is a non-asymmetrical cyanide dye.

10. A kit comprising a plurality of reagents to make a biological assay mixture for multiplexed bacterial strains detection, the reagents comprising:
  (a) a universal Gram-positive forward and reverse primer pair consisting of SEQ ID NO: 1 and 2, respectively; and
  (b) a universal Gram-negative forward and reverse primer pair consisting of SEQ ID NO: 3 and 4, respectively;
  (c) at least two biological probes comprising at least one fluorophore each, wherein at least one biological probe comprises a sequence selected from SEQ ID NOS: 11-15 that is configured to detect an amplicon of the gene hrcA prepared by the Gram-positive forward and reverse primer pair, and at least one biological probe comprises a sequence selected from SEQ ID NOS: 5-10 and configured to detect an amplicon of the gene lolB prepared by the Gram-negative forward and reverse primer pair; and
  (d) at least one oligonucleotide intercalating dye able to be used in a High Resolution Melt Analysis (HRMA);
  wherein the biological assay mixture is able to identify a plurality of Gram-positive and Gram-negative bacterial strains concurrently in a Real-Time Polymerase Chain Reaction (PCR); and
  if Real-Time PCR fails to identify a bacterial strain, the biological assay mixture is still able to detect the presence of a plurality of Gram-positive and Gram-negative bacteria strains within a patient's specimen by HRMA analysis.

11. The kit of claim 10, wherein the at least two biological probes comprise,
  (a) at least one probe with one fluorophore emitting light at a distinct emission wavelength; and
  (b) at least one probe with two or more fluorophores, wherein the fluorophores have resolvable distinct emission wavelengths.

* * * * *